United States Patent [19]

Chapman

[11] 4,000,212

[45] Dec. 28, 1976

[54] UNITARY ACID-HYDROCARBON REACTOR IN HYDROCARBON ALKYLATION

[75] Inventor: Charles C. Chapman, Bartlesville, Okla.

[73] Assignee: Phillips Petroleum Company, Bartlesville, Okla.

[22] Filed: July 22, 1975

[21] Appl. No.: 598,511

Related U.S. Application Data

[63] Continuation of Ser. No. 167,333, July 29, 1971, abandoned.

[52] U.S. Cl. .................. 260/683.45; 260/683.42; 260/683.48
[51] Int. Cl.² ........................................ C07C 3/54
[58] Field of Search ............... 260/683.48, 683.43, 260/683.58, 683.59, 671 R, 683.45, 683.42, 666 P

[56] References Cited

UNITED STATES PATENTS

| | | | |
|---|---|---|---|
| 2,386,681 | 10/1945 | Hadden | 260/683.48 |
| 2,412,863 | 12/1946 | Bolinger et al. | 260/683.48 |
| 2,937,079 | 5/1960 | Van Pool | 260/683.48 |
| 3,133,128 | 5/1964 | McDonald | 260/683.59 |

*Primary Examiner*—George Crasanakis

[57] ABSTRACT

A unitary acid-hydrocarbon reactor suitable for alkylation of hydrocarbons comprising, in a vertically disposed vessel, a lower acid-hydrocarbon mixing section, a reactor riser extending substantially centrally of the vessel from a top portion of said section, an upper acid-hydrocarbon settling section, the reactor riser extending to a midportion of said section, means below the upper end of said reactor riser for removing settled acid from said settling section, means for cooling said acid, means for returning said acid to the vessel to said mixing section, means for injecting hydrocarbon into said mixing section for admixture with acid therein, individual mixing compartments open at their upper and lower ends disposed within said mixing section disposed for acid flow upwardly therethrough and at least one nozzle in each of said compartments for injecting hydrocarbon into the acid flowing therethrough, each compartment being of a length extending upwardly from its nozzle sufficient to permit substantial mixing of the acid and hydrocarbon therein and to constrain turbulence created by said mixing within said compartment so as not to interfere with the turbulence or mixing in an adjacent compartment.

7 Claims, 7 Drawing Figures

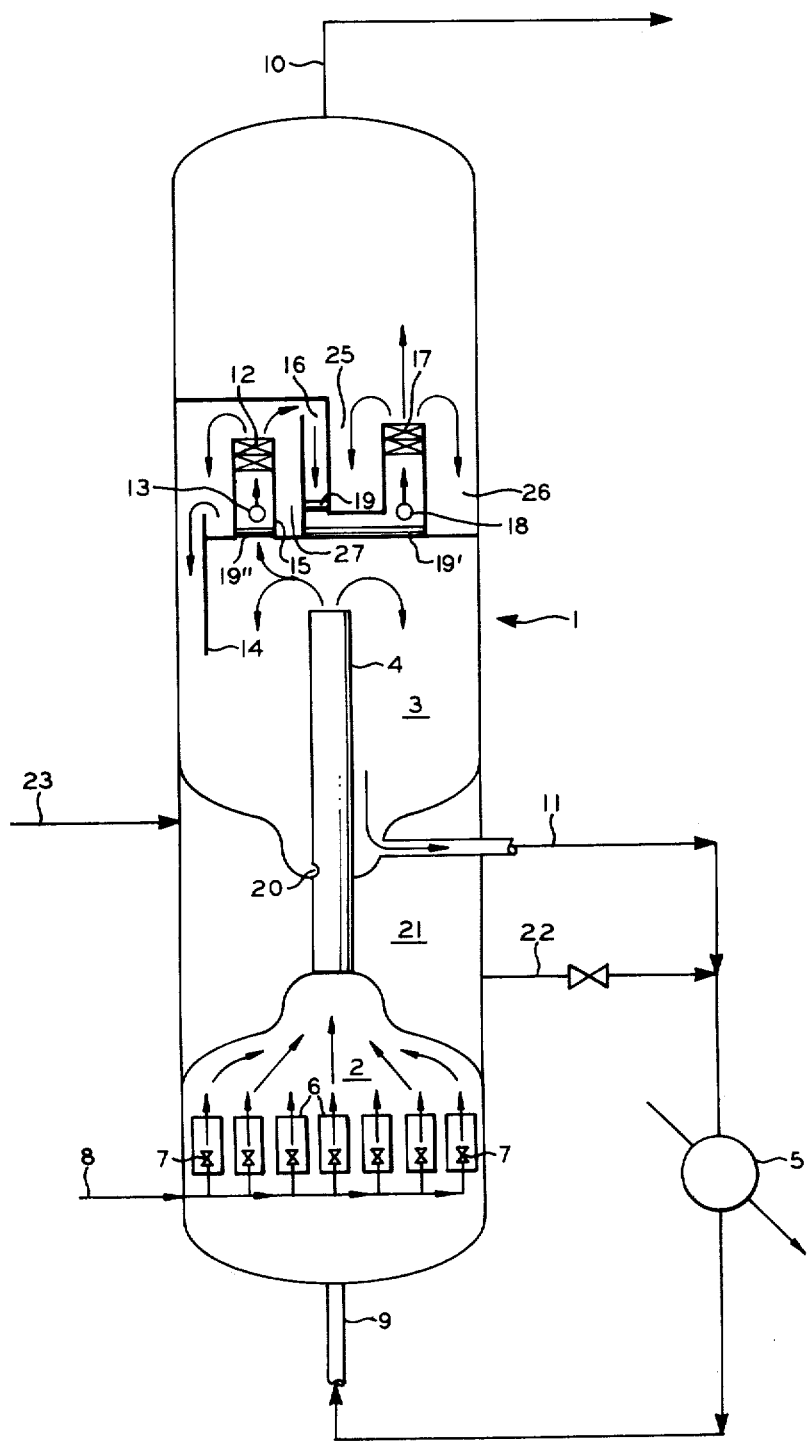
FIG. 1
INVENTOR.
C.C. CHAPMAN
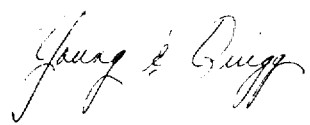
ATTORNEYS

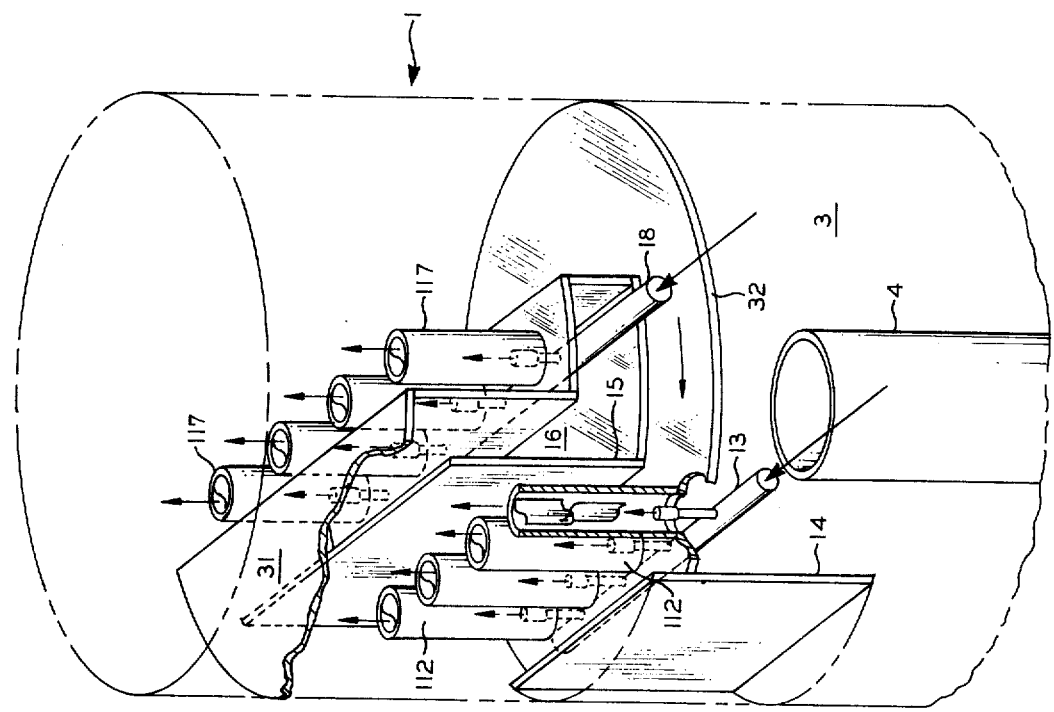
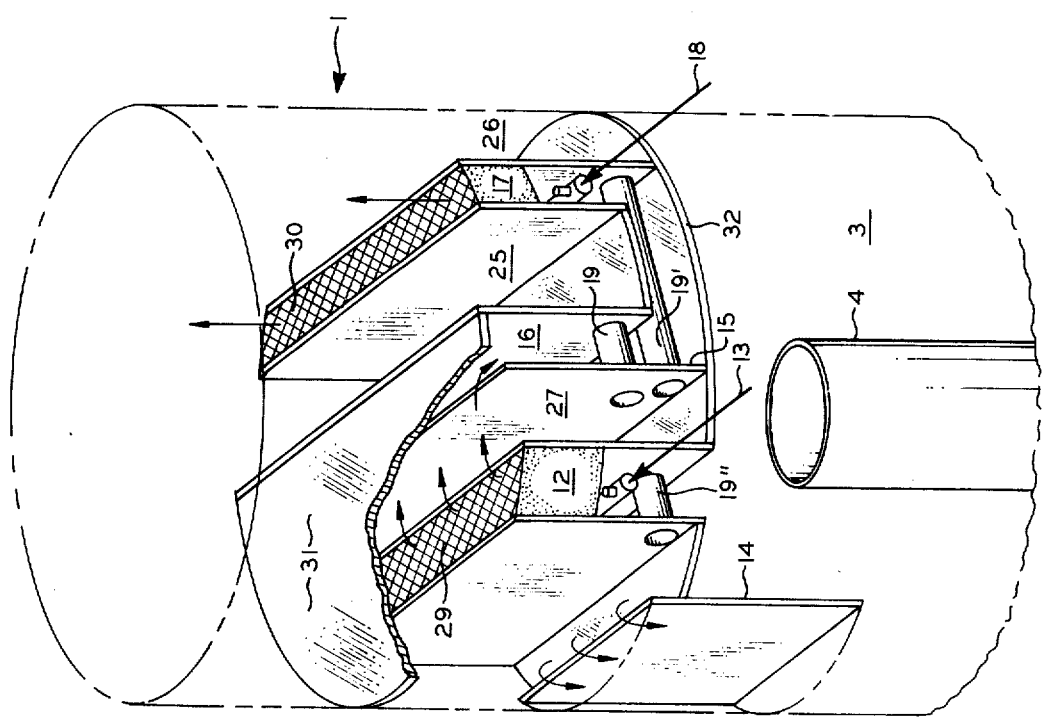

INVENTOR.
C.C. CHAPMAN

BY

ATTORNEYS

UNITARY ACID-HYDROCARBON REACTOR IN HYDROCARBON ALKYLATION

This is a continuation application of my copending application having Ser. No. 167,333, filed July 29, 1971, now abandoned.

This invention relates to an acid-hydrocarbon reactor. It also relates to a method for reacting hydrocarbons in the presence of an acid. In one of its aspects, the invention relates to a reactor apparatus comprising, in combination, an acid-hydrocarbon mixing means, a riser-reactor and acid from hydrocarbon settling means. In another of its aspects, the invention relates to a method for the alkylation of hydrocarbons in the presence of an acid catalyst.

In one of its concepts, the invention provides a unitary vessel having a bottom acid-hydrocarbon mixing section, a top acid-hydrocarbon settling section, a reactor riser extending from an upper portion of said mixing section to an intermediate portion of said acid-hydrocarbon settling section, means for removing separated hydrocarbon from said settling section, means for removing acid from said settling section, means for returning acid to the vessel and to said mixing section, means for introducing hydrocarbon to said mixing section, means within said mixing section forming individual compartments adapted for acid flow upwardly therethrough and individual nozzle means for injecting into acid flowing upwardly through each of said compartments hydrocarbon for admixture with acid in each of said compartments, said compartments forming a grid-like or honeycomb-like structure of sufficient depth along the line of acid and hydrocarbon flow to constrain or to confine turbulence resulting from admixture of hydrocarbon and acid within the compartment until substantially complete mixing has been accomplished, thus avoiding that turbulence created in one compartment shall interfere with turbulence created in another compartment.

In another of its concepts, the invention provides a method for the alkylation of a hydrocarbon with another hydrocarbon, for example, an isoparaffin with an olefin in the presence of an acid e.g. hydrofluoric acid catalyst, which comprises introducing into a lower mixing zone comprising a plurality of upwardly extending individual mixing sub-zones acid catalyst into each of said sub-zones for flow upwardly therethrough, also introducing into each of said sub-zones hydrocarbons to be alkylated, the hydrocarbons to be alkylated being introduced into each of said sub-zones with a force and in a state of energy such that considerable turbulence is created in each of said sub-zones, each of said sub-zones being of a sufficient length along the line of flow of acid and hydrocarbon mixing therein that the mixing is substantially completed while hydrocarbon and acid is confined in each of said sub-zones thus to avoid any substantial interference by turbulence created in one sub-zone with turbulence created in any other sub-zone, then intermingling acid and hydrocarbon mixture resulting from each of said sub-zones, flowing a final admixture thus obtained upwardly through a substantially vertically extending reaction zone into an acid from hydrocarbon settling zone, in said settling zone separating acid and hydrocarbon, removing hydrocarbon product, withdrawing acid from said settling zone, cooling said acid, and returning said acid to said first mentioned zone.

In a further concept, the invention provides an apparatus, as herein described, further characterized in that in the acid settling section there is provided an upper sub-section comprising means for introducing additional, preferably stronger, fresh acid for contact with separated hydrocarbon or alkylate therein.

In still a further concept of the invention, there is provided a method for contacting separated alkylate in the upper portion of the hydrocarbon-acid separation or settling zone with additional, preferably stronger, fresh acid of a kind and character such that the alkyl fluorides which result when hydrofluoric acid is the catalyst will be converted to additional valuable alkylate.

The art of alkylation is replete with various and different forms of apparatus and with various and different methods for better bringing about the alkylation of hydrocarbon. Indeed, the importance of improved octane value or number, especially at a time when low-lead or lead-free gasoline or fuels are of increasing importance cannot be stressed too much. Also, in a highly competitive field, such as the motor fuel industry is, economy of operation is essential. Better apparatus and better methods of contacting have been sought avidly in the alkylation art.

As appears from a consideration of this disclosure, the drawing and the appended claims, I have conceived of a better apparatus and method of contacting acid and hydrocarbon. Also, I have conceived of a combination or unitary apparatus wherewith to do so. Further still, I have conceived of a combination of apparatus components and a corresponding combination of method steps not only for the improved handling of the alkylation, per se, but also for the removal or utilization of alkyl fluorides which are formed especially in some types of operation.

An operation in which the alkylation of an isoparaffin with an olefin is accomplished and in which under some circumstances there are formed alkyl fluorides is described in Ser. No. 79,405 filed Oct. 12, 1970, continuation-in-part Ser. No. 138,991 filed Apr. 30, 1971, now U.S. Pat. No. 3,761,540.

In that application there is described and claimed a process for the alkylation of at least one isoparaffin with ethylene which comprises conducting the alkylation with intimate admixture of the reactants and hydrogen fluoride alkylation catalyst in the presence of a substantial amount of a higher olefin. The disclosure of said application for patent is incorporated herein by reference.

The concepts of the present invention are applicable also to other alkylations of one hydrocarbon by another in the presence of an acid catalyst.

An object of this invention is to provide for the more efficient contacting of reactants with a fluid catalyst. Another object of the invention is to provide for the better handling of hydrocarbon-acid catalyzed-alkylations. A further object of the invention is to provide an apparatus for contacting hydrocarbons to be alkylated with an acid catalyst. A still further object of the invention is to provide a method for the alkylation of hydrocarbons in the presence of an acid catalyst. Further, another object of the invention is to provide an apparatus in which mixing of acid and hydrocarbons to be alkylated can be accomplished effectively with turbulence. Another object still of the invention is to provide a unitary apparatus in which turbulence of mixing is controlled. A further object still is to accomplish in the mixing of hydrocarbons to be alkylated with acid catalyst, the best possible conditions of turbulence for mixing and to preserve these conditions until mixing has been substantially completely accomplished. Another object of the invention is to provide method and apparatus wherein in a single operation after treatment of alkylate produced to remove or to utilize therein alkyl fluorides which may have been formed can be accomplished.

Other aspects, concepts, objects and the several advantages of the invention are apparent from the study of this disclosure, the drawing and the appended claims.

According to the present invention, a unitary form of apparatus is provided which essentially comprises a substantially upright vessel, the vessel being divided into three sections, a lower acid and hydrocarbon mixing section, an upper alkylate-acid separation or settling section, and an intermediate reactor riser, the reactor riser communicating with the mixing section and the settling section and extending to a point above the base of the settling section, the settling section having means at its base for removing settled acid therefrom and at an upper portion thereof means for removing alkylate from the vessel.

Also according to the invention, the unitary apparatus as described, in the settling section in an upper portion thereof is provided with means for further contacting separated alkylate with additional acid, as described herein.

The apparatus of the present invention is particularly applicable to small alkylation units. However, any size desired can be constructed and operated as herein described.

In the drawing,

FIG. 1 is a vertical cross-sectional view of the simplified form of the apparatus.

FIG. 2 is an isometric view of an embodiment of the top section of the diagramatically shown apparatus of FIG. 1 and shows in some detail the path of flow of the upwardly rising hydrocarbon as it is admixed with the acid and as it passes through the open space between 15 and 19 of FIG. 1. This structure is a feature of the invention in that it permits considerable contacting within the upper section of the tower.

FIG. 2A shows another modification of the tower top contacting section in cutaway isometric view. This embodiment is also a feature of the invention.

Figure 3:
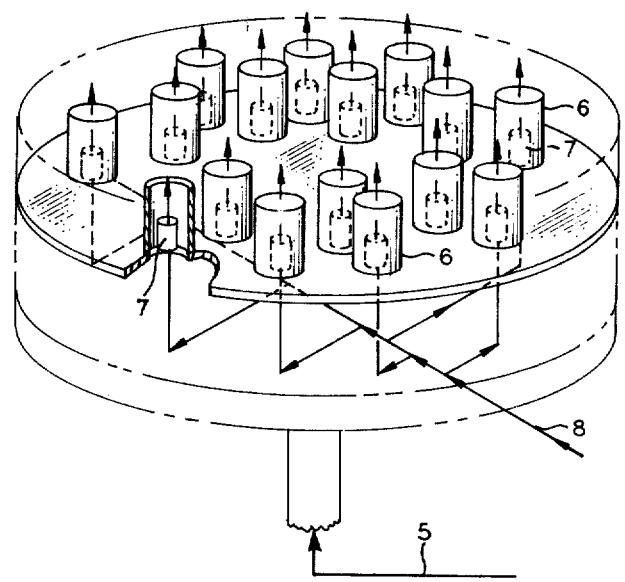
FIGS. 3, 4, 5 and 6 show respectively the lower section in part cutaway of the apparatus of the invention to arrangements of a part planned view thereof.

Referring now to FIG. 1 there is provided in vessel 1, which preferably is elongated, an acid-hydrocarbon mixing section 2 and a settling section 3 connected by reactor riser pipe 4. Acid from cooler 5 enters vessel 1 by pipe 9 and passes upwardly through structure 6.

Structure 6 provides, according to a concept of the invention, separate mixing compartments and can be constructed in any form as long as separate mixing compartments or sub-divided mixing can take place therein. In a presently preferred form of the invention, section 6 comprises juxtaposed elongated rectangular compartments as can be better seen in FIGS. 5 and 6. Each compartment is equipped with a nozzle 7 through which hydrocarbon is discharged into the rising acid for admixture therewith in each compartment. The hydrocarbon is introduced at 8.

The ratio and flow rates of the hydrocarbon, acid and the ultimate mixture can be various. Suffice to say the relative flow of hydrocarbon to acid should be sufficient so that the energy of introduction of the hydrocarbon into the acid will create instantaneously very good turbulence and consequent very good admixture of the acid and hydrocarbon.

As can be seen from the drawing and understood from this discription thereof each compartment permits very fine admixture to take place without the turbulence therein affecting or interfering with the turbulence or mixing taking place in adjacent compartments.

It is within the scope of this invention to adjust the relative dimensions of each of the compartments so as to affect favorably the mixing taking place therein. I am aware that the walls of the compartments will react against the turbulent mixture and that adjustment of the cross-sectional area and of the particular position of the nozzle or nozzles therein can be important.

The nozzles can be of the type described in U.S. Pat. No. 3,435,092 issued Mar. 25, 1969, Thomas Hutson, Jr., and Cecil O. Carter. The disclosure of that patent is incorporated herein by reference.

It will be observed that the mixing can be so designed or adjusted that it will take place independently of the over-all velocity of flow from pipe 5 and ultimately from section 2 upwardly through riser-reactor 4.

Separated alkylate is taken off from settler section 3 at 10 and settled acid is withdrawn from section 3 by pipe 11.

In the upper portion of section 3 there are provided means for further contacting alkylate substantially separated from acid with further stronger or fresh acid as earlier described. The details of this further contacting means are better understood in conjunction with FIG. 2. Separated hydrocarbon rises as shown by the arrows through a number of contactor elements 12. The fresh acid enters at 13 for admixture with the hydrocarbon. Reaction takes place in elements 12 which act to contact and intermix the acid with the alkylate which contains alkyl fluoride, for example. The further reacted alkylate and acid spill over the top of contactor element 12. Acid overflows and passes through downcomer 14. Hydrocarbon separating above the acid level passes over plate 15 and downwardly through intermediate section 16 into a further contacting element 17 wherein it is additionally contacted in a second fresh acid contacting step by acid introduced at 18. Acid separating from the effluent from the top of 17 passes through cross-over pipe 19 into the mass of acid surrounding contactor element 12. Thus, as described, there are two acid contactings in a series of contactors 12 and in a series of contactors 17. There may be one single structure such as contactor 12 in lieu of a series thereof. Also there may be one contactor means in lieu of 17. Further, although two contacting sections are shown there may be one or three or more such sections.

While the compartments have been shown to be rectangular elongate and in juxtaposition these compartments can be circular or of any desired shape or size or relative sizes. There is provided, according to the invention, a flexible tool wherewith to design for each operation the specific mixing which it demands for best results.

It will be observed that with the invention mixing means and method "hot spots" are substantially eliminated. Mixing is thorough and rapid and there can be handled a high volume of acid and hydrocarbon with considerably sub-divided mixing points in the enlarged section 2.

A weep hole 20 is provided for drainage during shutdown. The acid in 21 surrounds reactor riser 4 and assists in controlling the temperature of the reaction. Section 21 also acts as storage. Acid can be taken from section 21 by pipe 22 and passed to cooler 5. Make-up acid can be added to the system at 23. Acid added to the system at 13 and/or 18 admixes with acid emanating from reactor riser 4.

In FIG. 2, which is an isometric view of the upper portion of FIG. 1, the numbers used designate the same members or sections as in FIG. 1, wherein settling section 3 riser, reactor 4, contact elements 12, fresh acid entry 13, downcomer 14, plate 15, intermediate section 16, further contacting element 17 or recontact zone, and fresh HF acid entry 18 are depicted. Cross over pipes 19, 19', and 19", are shown in FIG. 1, pass settled HF acid from sections 25, 26, and 27, respectively to section 28 which communicate with HF acid downcomer 14. Contacting means, such as metal mesh, screen, or static mixers, are indicated at 29 and 30. Dividing means 31 prevents direct communication between the outlet of contact zone 12 and the hydrocarbon zone 17 thereabove. Plate 32 divides the recontact zone and the settling zone 3.

In FIG. 2A, which is another modification of FIG. 1, like members or sections use the same numbers that are used in FIG. 1, wherein settling section 3, reactor riser 4, fresh acid entries 13 and 18, downcomer 14, plate 15, intermediate section 16, and dividing means or plate 31 are depicted. Contacting elements 112 and 117 are substituted for contacting elements 12 and 17 of FIG. 1, and herein, in FIG. 2A, are open pipes containing mixing means such as static mixers, not shown, but such as illustrated in FIG. 2 and numbered 29 and 30 in FIG. 2.

FIG. 3 illustrates the lower section of the apparatus wherein 9 designates the HF acid entry, 6 illustrates circular cross-sectioned mixing compartments, 7 represents the nozzles from which the hydrocarbon feed 8 is expelled upwardly.

Figure 4:
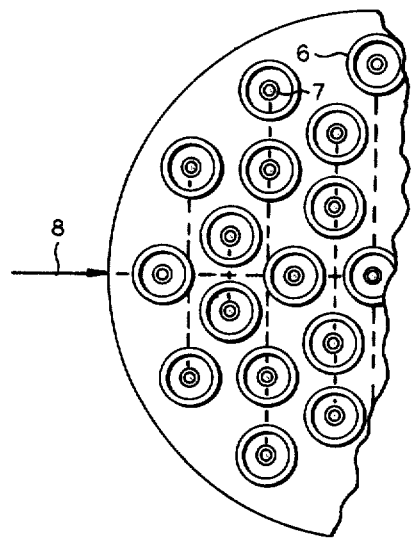

FIG. 4 is a cross section of FIG. 3.

Figure 5:
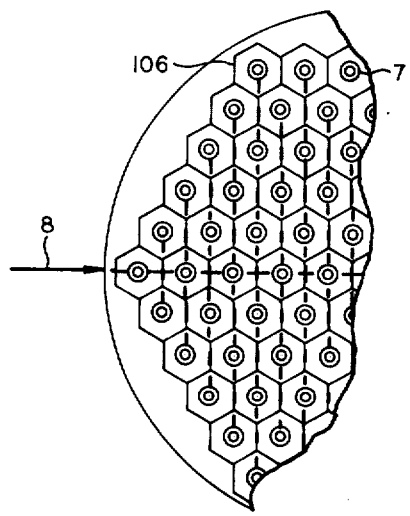

FIG. 5 shows hexagonal mixing compartments 106 in cross section, and hydrocarbon feed nozzles 7.

Figure 6:
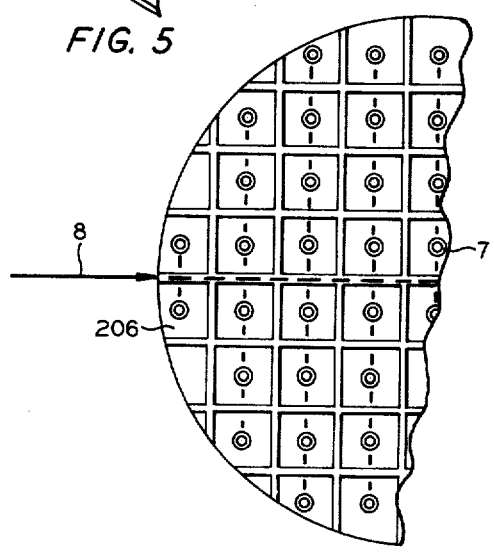

FIG. 6 shows square or rectangular mixing compartments 206 in cross section, and feed nozzles 7.

The following is an example of operation according to the present invention.

| | | |
|---|---|---|
| Hydrocarbon Feed (8): | | |
| Barrels/Day | | 32,450 |
| Volume Percent: | | |
| Propylene | 2.5 | |
| Propane | 5.3 | |
| Isobutane | 74.2 | |
| Butylenes | 3.5 | |
| Normal Butane | 12.6 | |
| C₅ Plus | 1.9 | |
| Hydrocarbon Product (10): | | |
| Barrels/Day | | 32,000 |
| Volume Percent: | | |
| Propane | 5.8 | |
| Isobutane | 68.4 | |
| Normal Butane | 12.9 | |
| Alkylate | 12.9 | |
| Organic Fluorides, (PPM WT) | | 100 |
| HF Catalyst (9) Charge to Main Reactor: | | |
| Barrels/Day | | 128,000 |
| Acid Strength (% WT) | | 92.0 |
| Hydrocarbon to First Recontact (12): | | |
| Barrels/Day | | 32,000 |
| Organic Fluorides, (PPM WT) | | 450 |
| HF Acid (13) to First Recontact (12): | | |
| Barrels/Day | | 200 |
| Acid Strength (% WT) | | 95 |
| Hydrocarbon to Second Recontact (17): | | |
| Barrels/Day | | 200 |
| Organic Fluorides, (PPM WT) | | 180 |
| HF Acid (18) to Second Recontact (17): | | |
| Barrels/Day | | 200 |
| Acid Strength (% WT) | | 99 |
| Main Reaction Zone (4 & 6): | | |
| Temperature, Avg., °F | | 90 |
| Pressure to Maintain Liquid Phases | | |
| Recontact Zones (12 & 17): | | |
| Temperature, Avg., °F | | 90 |
| Pressure to Maintain Liquid Phases | | |
| Total Cross Section of Main Contactors (6): | | |
| Square Feet | | 71.0 |
| Height of Main Contactors (6): | | |
| Feet | | 2.5 |
| Number of Main Contactors (6): | | 363 |
| Number of Nozzles (7): | | 363 |
| Size of Nozzle Orifice | | 3/16" Diam. |
| Total Cross Section of First Recontact (12): | | |
| Square Feet | | 1.5 |
| Height of First Recontact (12): | | |
| Feet | | 2.5 |
| Total Cross Section of Second Recontact (17): | | |
| Square Feet | | 1.5 |
| Height of Second Recontact (17): | | |
| Feet | | 2.5 |
| Each Orifice Size in Recontact Acid (13 & 18): | | 3/32" Diam. |
| Number of Orifices in Total Recontact: | | 24 |
| Main Riser (4) Diameter, Feet | | 2.7 Diam. |

| Main Riser (4) Length, Feet | 30.0 |
|---|---|

Olefins which can be charged to the alkylation system include ethylene and a heavier olefin such as propylene, butylene(s), and amylenes, or any one of propylene, butylene(s), and amylenes, or admixtures of these.

The isoparaffins which can be charged to the alkylation system include isobutane and isopentane, alone or in combination.

The preferred alkylation catalyst is hydrofluoric acid which can be between about 80 and 100 weight percent HF. preferably a small amount of water, up to about 5 weight percent, can be present in the HF acid.

The isoparaffin to olefin mol ratio is preferably about 4 1 to 1 up to about 20 to 1, or higher.

The volume ratio of HF catalyst to total hydrocarbon can run from about 1 to 2 to about 10 to 1.

Reasonable variation and modification are possible within the scope of the foregoing disclosure, drawings and the appended claims to the invention, the essence of which is that there has been provided a unitary apparatus in which acid and hydrocarbon are contacted in sub-divided or separate or individual mixing compartments or sections in a controllable manner and in a manner to prevent turbulence in one compartment from affecting the turbulence or mixing taking place in another compartment and that a method has been set forth for employing the apparatus substantially as described herein.

I claim:

1. A method for the alkylation of a hydrocarbon with another hydrocarbon and in the presence of an acid catalyst which comprises introducing acid and a hydrocarbon mixture comprising both hydrocarbon alkylating agent and alkylatable hydrocarbon into an acid-hydrocarbon mixing zone, providing in said mixing zone a multiplicity of sub-zones, introducing said hydrocarbon mixture into each of said sub-zones with force, passing acid through each of said sub-zones to receive the introduced hydrocarbon mixture thereinto, maintaining the acid and hydrocarbon mixture thus admixed in each of said sub-zones in said sub-zones until mixing thereof has been substantially completed, then passing acid and hydrocarbon mixture thus admixed in each of said sub-zones from the individual sub-zones into intermingling relationship and upwardly into and through a riser-reaction zone of relatively reduced cross sectional area then into an alkylate-acid separation zone of cross section relatively larger than said riser-reaction zone, in said alkylate-acid separation zone separating alkylate from acid, passing separated acid downwardly around said riser-reaction zone, passing separated alkylate hydrocarbon from said alkylate-acid separation zone upwardly through an acid contacting reaction zone and then into an upper alkylate-acid separation zone, and recovering alkylate and acid from said last mentioned zone.

2. A method according to claim 1 wherein in said acid contacting reaction zone the separated alkylate hydrocarbon being passed upwardly therethrough is thoroughly admixed with upwardly introduced liquid acid catalyst in a manner to cause intimate admixture of said separated alkylate hydrocarbon with said upwardly introduced acid, the hydrocarbon and acid mixture thus obtained is allowed to settle, forming phases, an upper hydrocarbon phase is moved upwardly in the upper alkylate-acid separation zone, and acid phase is moved downwardly together with acid flowing downwardly around said riser-reaction zone.

3. A method according to claim 2 wherein at least a portion of the acid and hydrocarbon mixture, from which a substantial portion of acid has been settled, is passed from above a settled acid phase to a point outside the system.

4. The method of claim 1 wherein said hydrocarbon alkylating agent is at least one olefin and said alkylatable hydrocarbon is at least one isoparaffin.

5. The method of claim 4 wherein said olefin is chosen from among ethylene, propylene, butylenes, and amylenes and said isoparaffins are chosen from among isobutane and isopentane.

6. A method according to claim 4 wherein in said acid contacting reaction zone the separated alkylate hydrocarbon being passed upwardly therethrough is thoroughly admixed with upwardly introduced liquid acid catalyst in a manner to cause intimate admixture of said separated alkylate hydrocarbon with said upwardly introduced acid, the hydrocarbon and acid mixture thus obtained is allowed to settle, forming phases, an upper hydrocarbon phase is moved upwardly in the upper alkylate-acid separation zone, and acid phase is moved downwardly together with acid flowing downwardly around said riser-reaction zone.

7. A method according to claim 6 wherein at least a portion of the acid and hydrocarbon mixture, from which a substantial portion of acid has been settled, is passed from above a settled acid phase to a point outside the system.

* * * * *